United States Patent [19]

Wong

[11] 4,386,605
[45] Jun. 7, 1983

[54] CAPTURE AND RESTRAINING DEVICE

[76] Inventor: Albert Wong, 948 Micheltorena St., Los Angeles, Calif. 90026

[21] Appl. No.: 187,587

[22] Filed: Sep. 15, 1980

[51] Int. Cl.³ ............................................. A61F 5/37
[52] U.S. Cl. ..................................... 128/134; 119/151
[58] Field of Search ................. 128/134, 133; 5/82 R, 5/82 B, 89; 119/96, 151

[56] References Cited

U.S. PATENT DOCUMENTS

| 542,374 | 7/1895 | Sauerbier et al. | 5/82 X |
|---|---|---|---|
| 1,068,016 | 7/1913 | Stone | 5/82 |
| 1,639,424 | 8/1927 | Breslin | 128/134 |

FOREIGN PATENT DOCUMENTS 712542  9/1966  Italy ..................................... 128/134

*Primary Examiner*—Michael H. Thaler
*Attorney, Agent, or Firm*—Fulwider, Patton, Rieber, Lee & Utecht

[57] ABSTRACT

A capture and restraining device having two poles, at least one flexible strand extending between the poles, and retainers secured to the poles for slidably connecting the flexible strand to the poles. In one of the disclosed embodiments, the device has two strands forming continuous, closed loops. The first strand has two overlapping segments which run between the poles and two non-overlapping segments which run between the poles. The second strand has two non-overlapping segments which run between the poles and intertwine with the non-overlapping segments of the first strand. Each retainer includes a clasp fixedly secured to the pole and a ring through which the clasp and one or more of the flexible strands pass. The clasps may be releasable for releasably securing the rings to the poles. The device may further include straps with hand loops attached to the poles. Each pole may be comprised of a main pole section and longitudinal extension section detachably connected to the main pole section. In alternative disclosed embodiments of the invention, the flexible strands are interconnected and slidably connected to the poles in a variety of arrangements, and the device includes fewer and more flexible strands and additional components.

12 Claims, 12 Drawing Figures

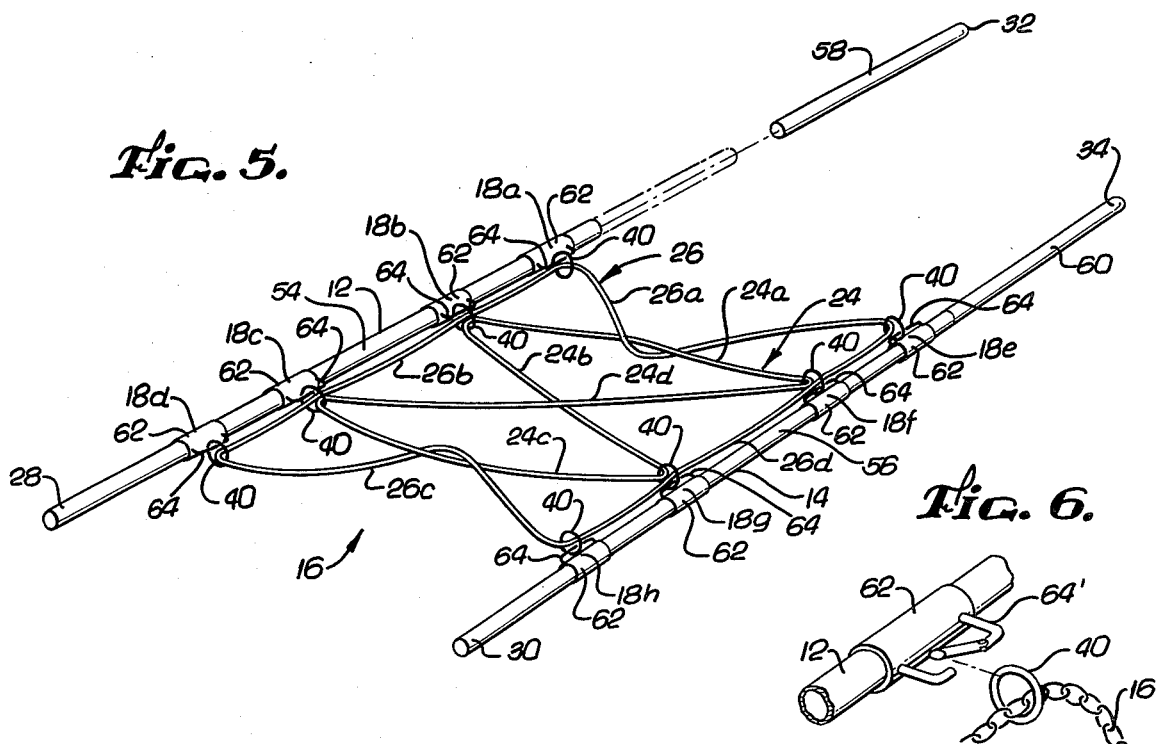
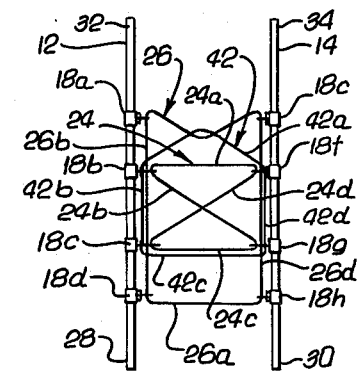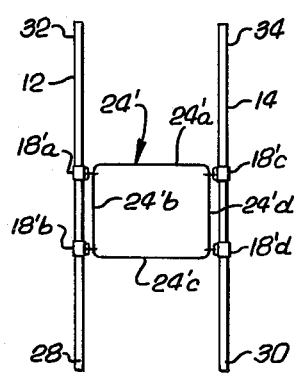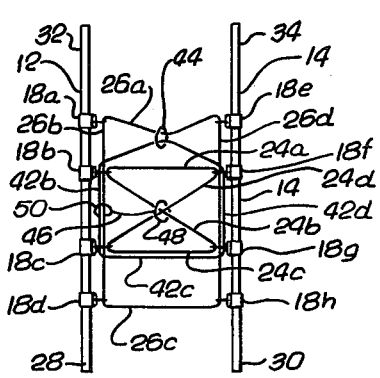
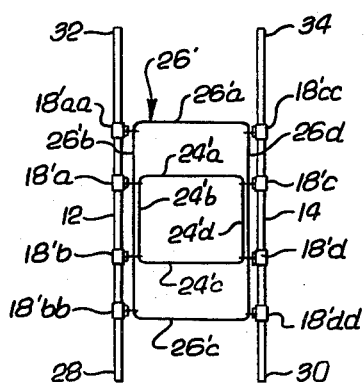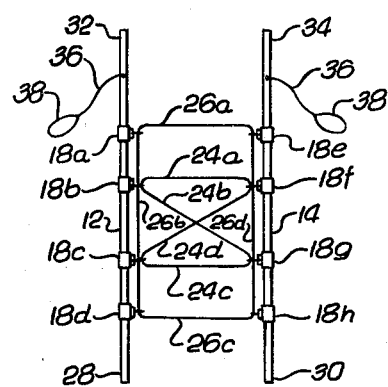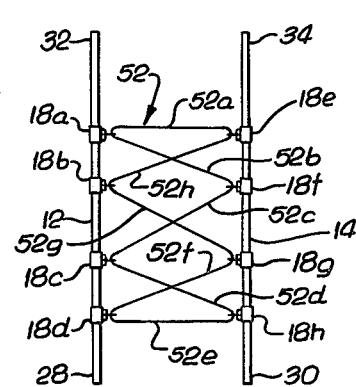

CAPTURE AND RESTRAINING DEVICE

BACKGROUND OF THE INVENTION

The present invention relates generally to capture and restraining devices and, more particularly, to a non-lethal device manually operated by two persons to safely capture and restrain individuals.

It is sometimes necessary for policemen and institutional custodians to capture and restrain violent or armed individuals. In the past, most such captures have been accomplished without the aid of any special equipment, other than a billie club or night stick, and have required the policemen or custodians to be in close proximity with the subject to be captured. Once the subject was captured, sheer physical strength was necessary to keep him restrained until handcuffs, medication or some other securing means could be employed.

In certain situations, such as when the subject to be captured and restrained is under the influence of drugs or armed with a knife or club and is unwilling to surrender when confronted, the risk of bodily injury to the policemen or custodians is greatly increased. The risk in such situations can be so great, that resort is had to lethal weapons, endangering the life of the subject of the capture.

It will therefore be appreciated that there is a significant need for a non-lethal device which can be used to capture and restrain an individual with a minimum of risk of bodily injury to all involved. Ideally, such a device should permit the users to maintain a reasonably safe distance from the subject of the capture until he is at least partially immobilized, and then facilitate subduing and restraining of the subject without requiring hands to be placed directly on the subject. The device should also be simple to use, portable, rapidly deployable and inexpensive. The present invention fulfills this need, and further provides other related advantages.

SUMMARY OF THE INVENTION

The present invention resides in a non-lethal capture and restraining device having at least two poles, at least one or more flexible strands extending between the poles, and retaining means secured to the poles for connecting the flexible strands to the poles to permit the safe capture and restrain of an individual when being in close proximity with the individual is too dangerous. Basically, and in general terms, the flexible strands are comprised of a plurality of segments which run between and are slidably connected to at least one of the poles by the retaining means. The flexible strands permit the ends of the poles toward the individual that is being captured to be held widely spread apart when approaching the individual, and forced tightly closed to provide a pincerlike action around the individual when the strands are pulled taut.

More specifically, in the presently preferred embodiments of the invention, the flexible strands form continuous, closed loops with segments which are slidably interconnected and slidably connected to the poles in a variety of arrangements, and have overlapping, non-overlapping and intertwining segments which run between the poles. The segments slide relative to the poles to allow the angular disposition of the poles while keeping the flexible strands taut.

In one of the presently preferred embodiments, the device has two poles, and first and second flexible strands forming, respectively, first and second continuous, closed loops slidably connected to the poles by retaining means. The first strand has two overlapping segments which run between the poles and two non-overlapping segments which run between the poles. The second strand has two non-overlapping segments which run between the poles and intertwine with the non-overlapping segments of the first strand.

The retaining means include clasps secured to the poles and rings releasably secured to the clasps. The flexible strands pass through the rings. The device further includes a hand strap attached to each of the poles by which possession of the device may be maintained when it is thrown to accomplish a capture. To facilitate storage and transportation of the device, the poles may be comprised of main pole sections and longitudinal extension sections detachably connected to the main pole sections.

Other features and advantages of the invention will become apparent from the following detailed description, taken in conjunction with the accompanying drawings.

BRIEF DESCRIPTION OF THE DRAWINGS

FIG. 5 is an enlarged, perspective view of the device shown in FIG. 1 with detachable pole extension sections;

FIG. 6 is an enlarged, sectional, perspective view of a retainer used with the device shown in FIG. 1;

FIG. 7 is a front elevational view of an alternative embodiment of the device shown in FIG. 1;

FIG. 8 is a front elevational view of an alternative embodiment of the device shown in FIG. 1;

FIG. 9 is a front elevational view of an alternative embodiment of the device shown in FIG. 1;

FIG. 10 is a front elevational view of an alternative embodiment of the device shown in FIG. 1;

FIG. 11 is a front elevational view of an alternative embodiment of the device shown in FIG. 1; and FIG. 12 is a front elevational view of an alternative embodiment of the device shown in FIG. 1.

DETAILED DESCRIPTION

Figure 1:
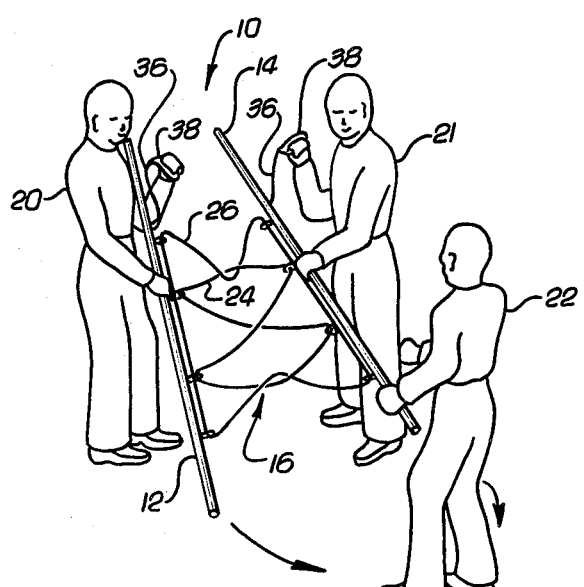
FIG. 1 is a perspective view of a capture and restraining device embodying the present invention, held in preparation for a capture.

As shown in the drawings for purposes of illustration, the present invention is embodied in a non-lethal capture and restraining device, indicated generally by reference numeral 10.

In accordance with the invention, the device 10 has a first pole 12 and a second pole 14, with one or more flexible strands, collectively referred to by reference numeral 16, extending between the poles and slidably connected thereto by a plurality of retainers 18 secured to the poles. The device 10 is constructed for operation by a pair of captors 20 and 21 and permits the safe capture and restraint of a combatant 22 in situations when being in close proximity with the combatant is too dangerous.

In one embodiment of the device 10, shown in operation in FIGS. 1-4, the flexible strands 16 include a first strand 24 and a second strand 26, with each forming a continuous, closed loop which is slidably connected to both the first and second poles 12 and 14 by the retainers 18 to permit the angular disposition of one pole relative to the other while keeping the flexible strands substantially taut. The loops formed by the flexible strands 24 and 26 are slidably interconnected. As will be described in more detail subsequently, the first and second strands 24 and 26 may be connected to the poles 12 and 14 and interconnected in a variety of arrangements, and the device 10 may include fewer or more flexible strands and additional components.

The device 10 is shown in FIG. 1 being held by the captors 20 and 21 in preparation for a leg capture of the combatant 22. The first and second poles 12 and 14 have first ends 28 and 30, respectively, which are held toward the combatant 22 and lowered, with the first ends widely spread apart. The poles 12 and 14 are held sufficiently separated to keep the strands 24 and 26 from drooping appreciably. The first and second poles 12 and 14 have second ends 32 and 34, respectively, which are held away from the combatant 22. A strap 36 is attached to each of the poles 12 and 14 toward its second end, and a hand loop 38 is formed by the strap at its unattached end. Each of the captors 20 and 21 holds his respective pole 12 and 14 in one hand, grasping the loop 38 of the strap 36 attached to his pole in the other hand.

The next step in the capture is to approach the combatant 22, and at an opportune moment, to position the first ends 28 and 30 of the poles 12 and 14, one to each side of and slightly behind the combatant. By using the strap 36, this step of the capture may be initiated at a greater distance from the combatant by permitting the poles 12 and 14 to be thrown forward by the length of the strap, the strap serving to maintain the captor's possession of the poles. The quickness of the throwing movement toward the combatant 22 allows rapid positioning of the poles 12 and 14, and adds an element of shock that aids in the capture. It will be appreciated, however, that the device 10 may be used without the straps 36 to capture a combatant.

Once the poles 12 and 14 are positioned to the sides of the combatant 22, each captors 20 and 21 grasps his pole, preferably with both hands, and moves it to cause the first ends 28 and 30 of the poles to come together and cross behind the combatant. With the poles 12 and 14 crossed, the captors 20 and 21 hold their repective poles, preferably toward their second ends 32 and 34, and pull the poles apart in generally opposite outward directions. This causes the strands 24 and 26 to become taut and to pull the first ends 28 and 30 of the poles 12 and 14 together, causing a pincerlike action which firmly grasps and holds the legs of the combatant 22 between the poles and the segments of the strands extending between the poles toward the first ends. With the legs of the combatant 22 held together and immobilized, locomotion is prevented and it is difficult for the combatant to maintain his balance if the struggles. The extent of the force applied to the poles 12 and 14, and where the captors 20 and 21 hold the pole when pulling them apart, determines the leverage involved and the amount of force the device 10 applies to the legs of the combatant 22.

Figure 2:
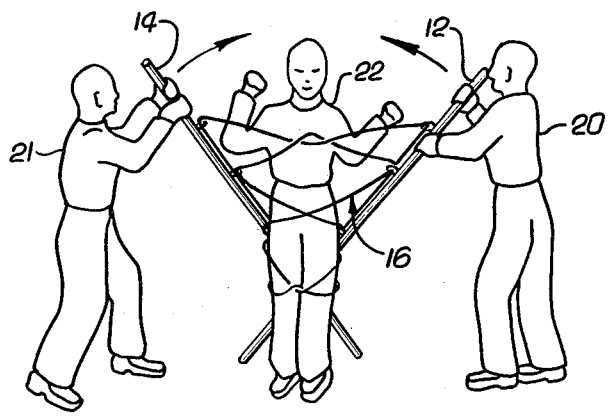
FIG. 2 is a perspective view of the device shown in FIG. 1 in operation.
Figure 3:
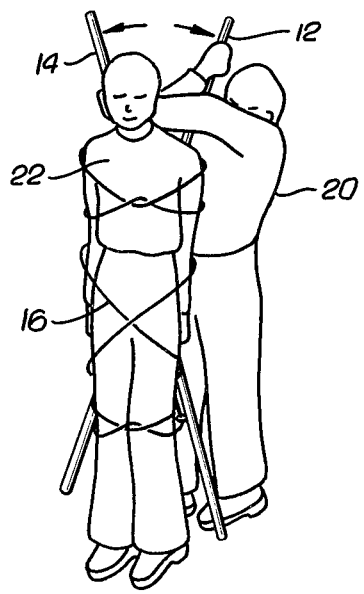
FIG. 3 is a perspective view of the device shown in FIG. 1 restraining an individual in an upright position.
Figure 4:
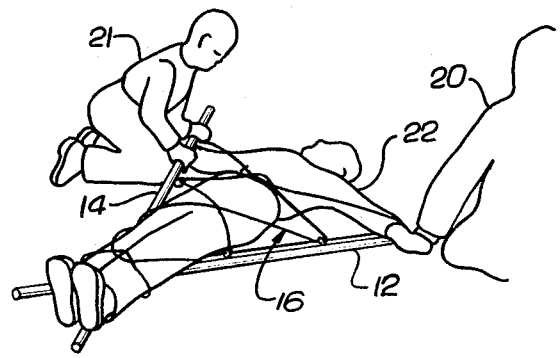
FIG. 4 is a perspective view of the device shown in FIG. 1 restraining an individual in a horizontal position.

The captors 20 and 21 may now, as shown in FIG. 2, raise the second ends 32 and 34 of the poles 12 and 14 upwardly and generally toward the combatant 22. When the poles 12 and 14 are raised to a substantially vertical position, the device 10 may be used to pin the combatant against a wall or wrapped around the combatant 22, to effectively restrain him in an upright position (see FIG. 3). Alternatively, the device 10 may be used to force the upper body of the combatant backwards, throwing him off balance and causing him to fall to the ground. Once the combatant 22 is on the ground, the device 10 may be used to pin the combatant's body to the ground, to effectly restrain him in a horizontal position (see FIG. 4).

The device 10 may also be used to accomplish a waist capture, which requires the first ends 28 and 30 of the poles 12 and 14 to be held at waist level and positioned one to each side of the combatant 22. The first ends 28 and 30 of the poles 12 and 14 are then brought together and crossed behind the combatant 22 at waist height. The second ends 32 and 34 of the poles 12 and 14 are then pulled in generally opposite outward directions by the captors 20 and 21 to provided a pincerlike action around the waist of the combatant 22. The waist capture keeps the legs of the combatant 22 free and allows the captors 20 and 21 to inhibit or direct the locomotion of the combatant by manipulating the second ends 32 and 34 of the poles 12 and 14 from a safe distance away from the combatant.

If the combatant 22 has one or both of his arms to his sides when the poles 12 and 14 are closed, the waist capture will also inhibit movement of the combatant's arms. It will be noted that in both the leg and waist captures, by having the strands 24 and 26 slidably connected to at least the first or second poles 12 or 14, the first ends 28 and 30 of the poles may be held widely spread apart when approaching the combatant, and forced tightly closed to provide a pincerlike action around the combatant when the strands are pulled taut.

In the embodiment of the device 10 described above in operation and shown in more detail in FIG. 5, the flexible strands 16 are slidably connected to the poles 12 and 14 by four retainers 18a–18d secured to the first pole and four retainers 18e–18h secured to the second pole. The first pole 12 has a first retainer 18a located inward from the second end 32 of the pole, and spaced therefrom in the direction of the first end 28 of the pole is a second retainer 18b. Spaced from the second retainer 18b in the direction of the first end 28 of the first pole 12 is a third retainer 18c, and spaced therefrom and inward from the first end 28 of the pole is a fourth retainer 18d. In similar fashion, the second pole 14 has a first retainer 18e located inward from the second end 34 of the pole, and spaced therefrom in the direction of the first end 30 of the pole is a second retainer 18f. Spaced from the second retainer 18f in the direction of the first end 30 of the second pole 14 is a third retainer 18g, and spaced therefrom and inward from the first end 30 of the pole is a fourth retainer 18h. Each of the retainers 18 includes a retainer ring 40 through which the flexible strands 16 pass.

More specifically, the first strand 24 forms a continuous, closed loop and has a segment 24a which runs between the second retainers 18b and 18f of the first and second poles 12 and 14, respectively, a segment 24b which runs between the second retainer 18b of the first pole and the third retainer 18g of the second pole, a segment 24c which runs between the third retainers 18c and 18g of the first and second poles, respectively, and a segment 24d which runs between the third retainer 18c of the first pole and the second retainer 18f of the second pole. The segments 24b and 24d overlap between the first and second poles 12 and 14.

The second strand 26 also forms a continuous, closed loop and has a segment 26a which runs between the first retainers 18a and 18e of the first and second poles 12 and 14, respectively, a segment 26b which runs between the first retainer 18a and the fourth retainer 18d of the first pole and is also connected to the first pole by the second retainer 18b and the third retainer 18c of the first pole, a segment 26c which runs between the fourth retainers 18d and 18h of the first and second poles, respectively, and a segment 26d which runs between the first retainer 18e and the fourth retainer 18h of the second pole and is also connected to the second pole by the second retainer 18f and the third retainer 18g of the second pole. The segment 24a intertwines with the segment 26a, and the segment 24c intertwines with the segment 26c.

A second embodiment of the device 10, illustrated in FIG. 11, has the same arrangement for the first and second strands 24 and 26 and the retainers 18a–18h as described above for the first embodiment, except that neither the segments 24a and 26a nor the segments 24c and 26c intertwine with each other. This embodiment is shown having the strap 36 with hand loop 38 attached to each of the poles 12 and 14 toward the second ends 32 and 34 of the poles.

A third embodiment of the device 10, illustrated in FIG. 7, has the same arrangement for the first and second strands 24 and 26 and the retainers 18a–18h as described above for the second embodiment, and further includes a third strand 42 having a segment 42a which runs between the second retainers 18b and 18f of the first and second poles 12 and 14, respectively, a segment 42b which runs between the second retainer 18b and the third retainer 18c of the first pole, a segment 42c which runs between the third retainers 18c and 18g of the first and second poles, respectively, and a segment 42d which runs between the second retainer 18f and the third retainer 18g of the second pole. The segment 26a of this embodiment interwines with the segment 42a.

A fourth embodiment of the device 10, illustrated in FIG. 9, has the same arrangement for the first, second and third strands 24, 26 and 42 and the retainers 18a–18h as described above for the third embodiment, except that the segments 26a and 42a do not intertwine with each other. Instead, in this embodiment the segments 26a is slidably attached to the segment 42a by a ring 44, through which both segments 26a and 42a pass. The ring 44 minimizes the drooping and entanglement that might otherwise occur when the strands 26 and 42 are not taut.

The device 10 of this fourth embodiment further includes a flexible fastening strand 46 having a ring 48 secured to one of its two ends, and a ring 50 secured to its other end. The segment 24b is slidably attached to the segment 24d by the ring 48, through which both segments pass. The segment 26b is slidably attached to the segment 42b by the ring 50, through which both segments pass, and the ring 50 is positioned between the second and third retainers 18b and 18c of the first pole 12. Such interconnection of the aforesaid segments of the first, second and third strands 24, 26 and 42 permits one of the captors 20 and 21 to increase the tautness of the strands, and hence the force of the pincerlike action of the device 10 when it is being used to restraint the combatant 22, by grasping and pulling on the fastening strand 46.

In a fifth embodiment of the device 10, illustrated in FIG. 8, a first strand 24' is slidably connected to the poles 12 and 14 by a pair of retainers 18'a and 18'b secured to the first pole 12 and spaced inwardly from the second and first ends 32 and 28 of the first pole, respectively, and by a pair of retainers 18'c and 18'd secured to the second pole 14 and spaced inwardly from the second and first ends 34 and 30 of the second pole, respectively. The first strand 24' forms a continuous, closed loop and has a segment 24'a which runs between the retainer 18'a of the first pole 12 and the retainer 18'c of the second pole 14, a segment 24'b which runs between the retainers 18'a and 18'b of the first pole, a segment 24'c which runs between the retainer 18'b of the first pole and the retainer 18'd of the second pole, and a segment 24'd which runs between the retainers 18'c and 18'd of the second pole.

A sixth embodiment of the device 10, illustrated in FIG. 10, has the same arrangement for the first strand 24' and the retainers 18'a–18'd as described above for the fifth embodiment, and further includes a second strand 26', a pair of retainers 18'aa and 18'bb secured to the first pole 12, and a pair of retainers 18'cc and 18'dd secured to the second pole 14. The retainer 18'aa is located between the second end 32 of the first pole 12 and the retainer 18'a, and is inwardly spaced from the second end. The retainer 18'bb is located between the first end 28 of the first pole 12 and the retainer 18'b, and is inwardly spaced from the first end. The retainer 18'cc is located between the second end 34 of the second pole 14 and the retainer 18'c, and is inwardly spaced from the second end. The retainer 18'dd is located between the first end 30 of the second pole 14 and the retainer 18'd, and is inwardly spaced from the first end.

The second strand 26' forms a continuous, closed loop independent of the first strand 24', and is slidably connected to the poles 12 and 14 by the retainers 18'aa–18'dd. The second strand 26' has a segment 26'a which runs between the retainer 18'aa of the first pole 12 and the retainer 18'cc of the second pole 14, a segment 26'b which runs between the retainers 18'aa and 18'bb of the first pole and is also slidably connected to the first pole by the retainers 18'a and 18'b of the first pole, a segment 26'c which runs between the retainer 18'bb of the first pole and the retainer 18'dd of the second pole, and a segment 26'd which runs between the retainers 18'cc and 18'dd of the second pole and is also slidably connected to the second pole by the retainers 18'c and 18'd of the second pole.

A seventh embodiment of the device 10, illustrated in FIG. 12, has the same arrangement for the retainers 18a–18h as described above for the first embodiment illustrated in FIG. 5, and has a strand 52 slidably connected to the poles 12 and 14 by the retainers. The strand 52 forms a continuous, closed loop and has a segment 52a which runs between the first retainers 18a and 18e of the first and second poles 12 and 14, respectively, a segment 52b which runs between the first retainer 18a of the first pole and the second retainer 18f of the second pole, a segment 52c which runs between the second retainer 18f of the second pole and the third retainer 18c of the first pole, a segment 52d which runs between the third retainer 18c of the first pole and the fourth retainer 18h of the second pole, a segment 52e which runs between the fourth retainers 18d and 18h of the first and second poles, respectively, a segment 52f which runs between the fourth retainer 18d of the first pole and the third retainer 18g of the second pole, a segment 52g which runs between the third retainer 18g of the second pole and the second retainer 18b of the first pole, and a segment 52h which runs between the second retainer 18b of the first pole and the first retainer 18e of the second pole. In this embodiment, the segments comprising each of the pairs of segments 52b and 52h, segments 52c and 52g, and segments 52d and 52f overlap between the first and second poles 12 and 14.

The device 10 of the present invention is of a sturdy and durable construction and is relatively inexpensive to manufacture. The poles 12 and 14 may be made of light-weight and resilient Teflon or fiberglass and have an approximate length of six feet, which has proven a satisfactory length for capturing and restraining a combatant 22 while still allowing the device 10 to fit into the trunk of an automobile. As illustrated in FIG. 5, to facilitate storage and transportation of the device 10, the poles 12 and 14 may be comprised of main pole sections 54 and 56, respectively, and longitudinal extension sections 58 and 60 detachably connected to the main pole sections 54 and 56, respectively. A conventional detent means (not shown) may be utilized for positioning and releasably holding the extension sections 58 and 60 in relation to the main pole sections 54 and 56. For convenience, the device 10 may be constructed to use the night sticks of policemen as the extension sections 58 and 60. Alternatively, device may be constructed with collapsable extension sections 58' and 60' (now shown) which telescope out from within the main pole sections 54 and 56. To avoid interference with the flexible strands 16 and retainers 18, the retainers are secured only to the main pole sections 54 and 56.

The flexible strands 16 may be made of chain, rope or leather strap, with chain having a link size of one-quarter inch to one-half inch being presently preferred. It is to be understood, however, that whenever the terms "flexible strand" and "strand" are used in the specification or claims herein, they are intended to include any suitable flexible connecting member.

In addition to the retainer ring 40, each of the retainers 18 has a base member 62 extending around and fixedly secured to one of the poles 12 and 14, and a generally "U" shaped clasp 64 fixedly secured to the base member and extending through the retainer ring 40 to slidably secure the ring to the base member. As illustrated in FIG. 6, the clasp 64 may be a clasp 64' of the selectively releasable type for releasably securing the retainer ring 40 to the base member 62.

Flexible strands 16 of a length sufficient to permit the poles to be separated by about three feet, when parallel and co-planar and with all retainers 18 utilized, has proven adequate in most situations. In certain embodiments, one releasable clasp 64' is provided at the first end 28 of the first pole 12 to allow selective adjustment of the distance the first ends 28 and 30 of the poles 12 and 14 may be separated by releasing the retainer ring 40 from the clasp. Releasable clasps 64' may be used throughout the device 10 to permit the flexible strands 16 to be quickly replaced with other flexible strands having a alternative arrangement that better suits the immediate purpose for which the device is going to be used. Such use of releasable clasps 64' would also allow easy replacement of worn or broken flexible strands 16.

It should be noted that although the flexible strands 16 have been described herein as forming continuous, closed loops, in certain embodiments of the device 10, a strand with an open loop secured at both ends to either the first pole 12 or the second pole 14 and slidably connected to the opposite pole, would operate in a manner substantially similar to a closed loop strand slidably connected to both poles. Although not preferred, the device 10 could be operated with one or more of the the flexible strands 16 being fixedly secured to both of the poles 12 and 14.

An incidental use (not illustrated) for the device 10 is as a barricade for crowd control. For such use, the poles 12 and 14 would be held vertically and either parallel or separated at one end or the other. With the poles 12 and 14 pulled apart to make the flexible strands 16 taut, the device functions as a fense, with the added advantage that should a member of the crowd become unruly, the device 10 may be readily employed as a capture and restraining device.

From the foregoing, it will be appreciated that the invention, as described herein for purposes of illustration, provides a non-lethal capture and restraining device which can be used to safely capture and restrain violent or armed individuals when being in close proximity with the individual is too dangerous. The device of the invention is not difficult to operate with a minimum of training, may be transported in the trunk of an automobile and easily carried by one person, can be quickly set up for operation, is sturdy and durable, and is inexpensive to manufacture. It will also be appreciated that, although specific embodiments of the invention have been described herein for purposes of illustration, various modifications may be made without departing from the spirit and scope of the invention. Accordingly, the invention is not limited except as by the appended claims.

I claim:

1. A portable capture and restraining apparatus comprising:

first and second poles, said poles being independently and angularly movable relative to each other;

a first flexible strand extending between said poles and forming a loop slidably connected to at least one of said poles;

a second flexible strand extending between said poles and forming a loop slidably connected to at least one of said poles, said second strand substantially encircling said first strand;

retaining means secured to said poles for connecting said flexible stands to fixed positions along said poles, said retaining means including first, second, third and fourth retainers secured to and sequentially spaced over each of said first and second poles; said first strand including a segment which runs between said second retainer of said first pole and said third retainer of said second pole, and a segment which runs between said third retainer of said first pole and said second retainer of said second pole; and said second strand including a segment which runs between said first retainers of said first and second poles, and a segment which runs between said fourth retainers of said first and second poles; and said first strand further including a segment which runs between said second retainers of said first and second poles and slidably intertwines with said segment of said second strand which runs between said first retainers of said first and second poles, and a segment which runs between said third retainers of said first and second poles and slidably intertwines with said segment of said second strand which runs between said fourth retainers of said first and second poles.

2. A portable capture and restraining apparatus comprising:

first and second poles, said poles being independently and angularly movable relative to each other and each having first, second, third and fourth retainers secured thereto and sequentially spaced thereover; and a plurality of flexible strands extending between said poles and connected thereto by said retainers, said strands including a first strand having a segment which runs between said second retainers of said first and second poles, a segment which runs between said second retainer of said first pole and said third retainer of said second pole, a segment which runs between said third retainers of said first and second poles, and a segment which runs between said third retainer of said first pole and said second retainer of said second pole, and a second strand having a segment which runs between said first retainers of said first and second poles, a segment which runs between said first and fourth retainers of said first pole, a segment which runs between said fourth retainers of said first and second poles, and a segment which runs between said first and fourth retainers of said second pole.

3. The apparatus of claim 2, wherein said retainers include at least one clasp connected to a ring through which at least one of said plurality of flexible strands pass.

4. The apparatus of claim 3, wherein said clasp is releasable for releasably securing said ring to one of said poles.

5. The apparatus of claim 2, wherein said apparatus further includes a hand strap attached to each of said pole.

6. The apparatus of claim 2, wherein each of said poles includes a main pole section and a longitudinal extension section detachably connected to said main pole section.

7. The apparatus of claim 2, wherein said segment of said first strand which runs between said second retainers of said first and second poles slidably intertwines with said segment of said second strand which runs between said first retainers of said first and second poles, and said segment of said first strand which runs between said third retainers of said first and second poles slidably intertwines with said segment of said second strand which runs between said fourth retainers of said first and second poles.

8. The apparatus of claims 2 or 7, wherein said first and second strands are slidably connected to at least said first pole by said retainers of said first pole.

9. The apparatus of claim 2, wherein said plurality of flexible strands further includes a third strand having:
a segment which runs between said second retainers of said first and second poles and intertwines with said segment of said second strand which runs between said first retainers of said first and second poles,
a segment which runs between said second and third retainers of said first pole,
a segment which runs between said third retainers of said first and second poles, and
a segment which runs between said second and third retainers of said second pole.

10. The apparatus of claim 2, wherein said apparatus further includes attached means, and said plurality of flexible strands includes a third strand having:
a segment which runs between said second retainers of said first and second poles and is slidably attached to said segment of said second strand which runs between said first retainers of said first and second poles by said attachment means,
a segment which runs between said second and third retainers of said first pole,
a segment which runs between said third retainers of said first and second poles, and
a segment which runs between said second and third retainers of said second pole.

11. The apparatus of claims 9 or 10, wherein said first, second and third strands are slidably connected to at least said first pole by said retainers of said first pole.

12. The apparatus of claim 10, further including a flexible fastening strand having fastening means secured to each of its two ends, said fastening means at said one end slidably fastening together said segment of said first strand which runs between said second retainer of said first pole and said third retainer of said second pole with said segment of said first strand which runs between said second retainer of said second pole and said third retainer of said first pole, and said fastening means at said other end slidably fastening together said segment of said second strand which runs between said first and fourth retainers of said first pole with said segment of said third strand which runs between said second and third retainers of said first pole.

* * * * *